(12) United States Patent
Hentrich et al.

(10) Patent No.: US 10,952,941 B2
(45) Date of Patent: Mar. 23, 2021

(54) HAIR TREATMENT AGENTS WITH HYDROPHOBIC FUMED SILICA

(71) Applicant: Henkel AG & Co. KGaA, Duesseldorf (DE)

(72) Inventors: Dirk Hentrich, Hamburg (DE); Lena Isabella Joost, Hamburg (DE); Elisabeth Poppe, Hamburg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 140 days.

(21) Appl. No.: 15/839,852

(22) Filed: Dec. 13, 2017

(65) Prior Publication Data
US 2018/0177691 A1    Jun. 28, 2018

(30) Foreign Application Priority Data

Dec. 22, 2016   (DE) .................... 10 2016 225 962.8

(51) Int. Cl.
| | | |
|---|---|---|
| *A61K 8/25* | (2006.01) | |
| *A61Q 5/12* | (2006.01) | |
| *A61K 8/42* | (2006.01) | |
| *A61Q 5/02* | (2006.01) | |
| *A61K 8/41* | (2006.01) | |

(52) U.S. Cl.
CPC ................ *A61K 8/25* (2013.01); *A61K 8/416* (2013.01); *A61K 8/42* (2013.01); *A61Q 5/02* (2013.01); *A61Q 5/12* (2013.01); *A61K 2800/596* (2013.01)

(58) Field of Classification Search
CPC ........... A61K 8/25; A61K 8/416; A61K 8/42; A61K 2800/596; A61Q 5/02; A61Q 5/12
See application file for complete search history.

(56) References Cited

U.S. PATENT DOCUMENTS

| | | | | |
|---|---|---|---|---|
| 2003/0108501 A1* | 6/2003 | Hofrichter | ............. | A61K 8/044 424/70.1 |
| 2006/0246027 A1 | 11/2006 | Tanner | | |
| 2011/0305652 A1* | 12/2011 | Hilvert | ................. | A61K 8/0295 424/59 |

FOREIGN PATENT DOCUMENTS

| | | | | |
|---|---|---|---|---|
| WO | 2009/021354 A1 | 2/2009 | | |
| WO | WO-2013064598 A2 * | 5/2013 | ........... | A61K 8/0241 |
| WO | 2013190027 A2 | 12/2013 | | |
| WO | 2016/000145 A1 | 1/2016 | | |

OTHER PUBLICATIONS

AEROSIL R 805, product information, hydrophobic fumed silica, Retrieved online [Jun. 22, 2020] (Year: 2019).*
Intellectual Property Office, Search Report under Section 17(5) for United Kingdom Patent Application No. GB1721358.8 date Sep. 27, 2018.

* cited by examiner

*Primary Examiner* — Nannette Holloman
(74) *Attorney, Agent, or Firm* — Lorenz & Kopf, LLP

(57) ABSTRACT

The present disclosure relates to cosmetic agents for cleaning and/or conditioning of hair, which, contain at least one hydrophobic fumed silica in addition to a specific combination of at least two different surfactants. These agents achieve an outstanding cleaning and/or conditioning performance and an increase in hair volume. Furthermore, the present disclosure relates to the use of at least one hydrophobic fumed silica in cosmetic agents for cleaning and/or conditioning of hair to increase the hair volume and/or improve lasting hold of the hair volume.

6 Claims, No Drawings

HAIR TREATMENT AGENTS WITH HYDROPHOBIC FUMED SILICA

CROSS-REFERENCE TO RELATED APPLICATION

This application claims priority to German Patent Application No. 10 2016 225 962.8, filed Dec. 22, 2016, which is incorporated herein by reference in its entirety.

TECHNICAL FIELD

The present disclosure relates to: a cosmetic agent for cleaning and/or conditioning of hair, which, contains at least one hydrophobic fumed silica in addition to a specific combination of at least 2 different surfactants. Use of the at least one hydrophobic fumed silica in these agents achieves an increase in hair volume and/or improved lasting hold of the hair volume without negatively influencing the texture and the cleaning and/or conditioning performance of these agents.

BACKGROUND

Furthermore, the present disclosure relates to the use of at least one hydrophobic fumed silica in cosmetic agents for cleaning and/or conditioning of hair to increase the hair volume and/or improve lasting hold of the hair volume.

Cosmetic agents for cleaning and/or conditioning of hair have been known for a long time and are regularly improved and/or adapted to changing requirements of consumers. For example, consumers expect a modern agent for cleaning and/or conditioning of hair to leave a long-lasting, haptically and optically perceptible nurturing effect on the hair. "Haptically and optically perceptible nurturing effect" is understood to mean that the hair is smooth, easy to comb, soft, shiny and easy to dress after the treatment. Furthermore, the treated hair should have an increased volume.

The addition of silicones and cationic polymers to agents for cleaning and/or conditioning of hair for improvement of the care is known in the prior art. The production and use of such agents, however, is currently problematic. On the one hand, some water-insoluble silicone types can often be dispersed in these agents only with increased energy consumption or using additional synthetic stabilizers over a prolonged period.

However, it was found that repeated use of such agents does not have any effect on the volume and has a greasy and weighted effect on damaged and/or very fine, thin hair types, in particular. Therefore, there is a continued requirement for agents for conditioning and/or cleaning of hair which can result in increased and long-lasting hair volume without negatively influencing the texture and cleaning and/or care effect.

The present disclosure addressed the problem of preparing agents for cleaning and/or conditioning of hair which gives the treated hair improved hair sensory characteristics and increased hair volume. In particular, damaged hair and/or very fine, thin hair cannot be knotted and/or made difficult to knot, easily untangled and supple after treatment with these agents. Furthermore, fine, smooth hair should have a long-lasting volume without a weighted effect after treatment. A further task of the present disclosure was to find compounds which increase hair volume that can be easily incorporated into the agents without negatively changing the texture or the cleaning and/or conditioning performance of the agents.

It has been found that the use of hydrophobic fumed silica in agents for cleaning and/or conditioning of hair achieves an increase in hair volume and/or extended lasting hold of the hair volume without negatively influencing the texture and cleaning and/or conditioning effect of these agents. Moreover, the addition of these silica does not reduce the storage stability of the cosmetic agents, so incorporation into existing formulations is possible without further complication.

BRIEF SUMMARY

Cosmetic agents and methods are provided herein. In an exemplary embodiment, a cosmetic agent for cleaning and/or conditioning of keratinous fibers comprises, in a cosmetically compatible carrier,
  a. at least one hydrophobic fumed silica,
  b. at least one surfactant (A) selected from the group of (i) alkyl(ether)sulfates having 8 to 18 carbon atoms in the alkyl chain and 1 to 6 ethylene oxide units, (ii) $C_{12}$-$C_{18}$-acyl isethionates, (iii) $C_{12}$-$C_{18}$-acyl sarcosinates, (iv) $C_{10}$-$C_{22}$-alkyl trimethylammonium chlorides, and (v) mixtures thereof, and
  c. at least one surfactant (B) selected from the group of (i) $C_{8-18}$-alkyl amido-($C_{1-4}$-alkyl)betaines, (ii) $C_{10}$-$C_{18}$-alkyl amphoacetates and -diacetates, (iii) $C_{10}$-$C_{18}$-alkyl polyglucosides, (iv) N-[3-dimethylamino-($C_{1-4}$-alkyl)]-$C_{12-18}$-alkanamides, (v) $C_{12}$-$C_{18}$-olefin sulfonates, and (vi) mixtures thereof.

In another exemplary embodiment, a method comprises using at least one hydrophobic fumed silica in cosmetic agents for cleaning and/or conditioning of hair to increase the hair volume and/or improve lasting hold of the hair volume.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

A first subject of the present disclosure, therefore, is a cosmetic agent for cleaning and/or conditioning of keratinous fibers in a cosmetically compatible carrier containing
  a) at least one hydrophobic fumed silica,
  b) at least one surfactant (A) selected from the group of (i) alkyl(ether)sulfates having 8 to 18 carbon atoms in the alkyl chain and 1 to 6 ethylene oxide units, (ii) $C_{12}$-$C_{18}$-acyl isethionates, (iii) $C_{12}$-$C_{18}$-acyl sarcosinates, (iv) $C_{10}$-$C_{22}$-alkyl trimethylammonium chlorides and (v) mixtures thereof and
  c) at least one surfactant (B) selected from the group of (i) $C_{8-18}$-alkyl amido-($C_{1-4}$-alkyl)betaines, (ii) $C_{10}$-$C_{18}$-alkyl amphoacetates and -diacetates, (iii) $C_{10}$-$C_{18}$-alkyl polyglucosides, (iv) N-[3-dimethylamino-($C_{1-4}$-alkyl)]-$C_{12-18}$-alkanamides, (v) $C_{12}$-$C_{18}$-olefin sulfonates and (vi) mixtures thereof.

Use of the at least one hydrophobic fumed silica in combination with a special combination of at least surfactants surprisingly achieves an increase in hair volume and/or improved lasting hold of the hair volume without negatively influencing the texture and the cleaning and/or conditioning performance of these agents. Furthermore, the aforementioned combination does not reduce the storage stability of these agents and can be incorporated into already existing formulations without further complication.

In the context of the present disclosure, the term "fumed silica" is understood to mean highly-dispersed silica, which are produced by employing flame hydrolysis. In the process, In this case, silicon tetrachloride is decomposed in an oxyhydrogen flame, wherein chain-like agglomerates with hydrophilic silanol groups form. Hydrophobically modified fumed silicas are obtained by employing a reaction of these silanol groups with organic reagents, for example organic amino or chlorosilanes.

Furthermore, in the scope of the present disclosure, the term "surfactants" is understood to mean amphiphilic (bifunctional) compounds including at least one hydrophobic and at least one hydrophilic molecule part. The hydrophobic radical is preferably a hydrocarbon chain with 8 to 28 carbon atoms, which can be saturated or unsaturated, linear or branched. It is especially preferable if this $C_8$-$C_{28}$ alkyl chain is linear. In this connection, the at least one first surfactant (A) differs from the at least one second surfactant (B).

The indication wt. % in this case, unless otherwise specified, refers to the total weight of the cosmetic agents as contemplated herein, where the sum of all the agents as contemplated herein is 100 wt. %.

The cosmetic agent contains components (a) to (c) in a cosmetically acceptable carrier.

Preferred cosmetically compatible carriers are aqueous carriers preferably having at least 10 wt. % water, relative to the total weight of the cosmetic agent.

It is particularly preferable that the cosmetically acceptable carrier contains water, particularly in a quantity that is preferably at least about 30 wt. %, more preferably at least about 50 wt %, particularly at least about 50 wt. % water relative to the total weight of the cosmetic agent. Particularly preferred cosmetic products, in relation to their total weight, have a water content of from about 55 to about 98 wt. %, more preferably from about 60 to about 97 wt. %, particularly from about 65 to about 95 wt. %.

The inventive cosmetic agent contains at least one hydrophobic fumed silica as a first essential component a).

As contemplated herein, however, preference is given to use of specific hydrophobic fumed silica. Therefore, advantageous cosmetic agents as contemplated herein are exemplified in that the hydrophobic fumed silica is modified with hexamethyldisilazane. In this context, the term "modified" is understood to mean the reaction of the hydrophilic fumed silica obtained from the flame hydrolysis of silicon tetrachloride with hexamethyldisilazane. Particular preference is given to use of hydrophobic fumed silica obtained, for example, by employing a hydrophilic fumed silicic acid produced by decomposing silicon tetrachloride in an oxyhydrogen flame and subsequent reaction with hexamethyldisilazane. Such silica are commercially available, for example, from Evonik under the trade name Aerosil® 812 S. Use of these silica results in a compound with the special surfactants (A) and (B) for an especially high and long-lasting hair volume without negatively influencing the texture, cleaning and/or conditioning effect, or the storage stability of the cosmetic agent as contemplated herein.

Furthermore, in the scope of the present disclosure, it has been found to be beneficial when the at least one hydrophobic fumed silica, particularly the hydrophobic fumed silica modified with hexamethyldisilazane has a specific surface. As contemplated herein, therefore, it is advantageous if the hydrophobic fumed silica has a specific surface (BET) of from about 130 to about 320 $m^2/g$, preferably from about 150 to about 300 $m^2/g$, more preferably from about 170 to about 280 $m^2/g$, particularly from about 190 to about 250 $m^2/g$. The specific surface can, for example, be determined by employing the method of gas absorption described in the European Pharmacopoeia (European Pharmacopoeia 5.1, chapter 2.9.26). With use of silica having the aforementioned specific surfaces, the hair volume and its lasting hold are further enhanced.

Furthermore, as contemplated herein it is advantageous if the at least one hydrophobic fumed silica, particularly the hydrophobic fumed silica modified with hexamethyldisilazane has a specific tamped density. Therefore, preferred embodiments of the inventive cosmetic agent are exemplified in that the hydrophobic fumed silica has a tamped density of from about 20 to about 100 g/l, preferably from about 30 to about 90 g/l, more preferably from about 40 to about 80 g/l, particularly from about 50 to about 70 g/l. The tamp density can, for example, be determined by employing the method described in the European Pharmacopoeia (European Pharmacopoeia 7.0, chapter 2.9.34). With use of silica having the aforementioned tamp densities, the hair volume and its lasting hold are further enhanced.

The hydrophobic fumed silica, particularly the fumed silica modified with hexamethyldisilazane having the aforementioned specific surface and tamp density is preferably contained in the inventive cosmetic agents in specific total amounts. As contemplated herein, it is therefore preferable for hydrophobic fumed silica to be contained in a total amount of from about 0.01 to about 5.0 wt. %, preferably from about 0.1 to about 4.0 wt. %, more preferable from about 0.3 to about 2.0 wt. %, particularly from about 0.5 to about 1.0 wt. %, relative to the total weight of the cosmetic agent. If a mixture of different hydrophobic fumed silica is used, these quantity specifications relate to the total amount of the mixture of silica. In the process, the increase and improvement of the lasting hold of the hair volume are already achieved with small amounts of hydrophobic fumed silica, particularly the fumed silica modified with hexamethyldisilazane having the aforementioned specific surface and tamp density. Furthermore, use of these silica in the aforementioned quantity ranges does not negatively influence the cleaning and/or conditioning effect of the cosmetic agents. Furthermore, the use of these total amounts of silica to not result in incompatibilities with other ingredients of the cleaning and/or conditioning agents so that incorporation into existing formulations is possible without further complication.

As a second and third essential ingredient, the cosmetic agent according to the present disclosure contains at least two different surfactants (A) and (B).

Surprisingly, it has been found that an outstanding, long-lasting increase of the hair volume and a good cleaning and/or conditioning effect are achieved if the cosmetic agent contains a specific combination of surfactants (A) and (B).

Therefore, a particularly preferred embodiment of the inventive cosmetic agent is exemplified in that the at least one first surfactant (A) is selected from sodium lauryl(ether) sulfate having 2 to 4 ethylene oxide units and the at least one second surfactant (B) is selected from $C_{8-18}$ alkylamidopropylbetaine and/or disodium-$C_{10}$-$C_{18}$-alkylamphodiacetate. This combination of surfactants achieves a particularly good cleaning effect without negatively influencing the hair volume achieved with the hydrophobic fumed silica or the long-lasting hold of the hair volume.

Therefore, an additional particularly preferred embodiment of the inventive cosmetic agent is exemplified in that the at least one first surfactant (A) is selected from sodium decyl (ether) sulfate having 2 to 4 ethylene oxide units and the at least one second surfactant (B) is selected from $C_{12}$-alkylamphodiacetate. This combination of surfactants also achieves a particularly good cleaning effect without negatively influencing the hair volume achieved with the hydrophobic fumed silica or the long-lasting hold of the hair volume.

Furthermore, an additional particularly preferred embodiment of the inventive cosmetic agent is exemplified in that the at least one first surfactant (A) is selected from $C_{12}$-$C_{18}$-acyl isethionates and the at least one second surfactant (B) is selected from $C_{10}$-$C_{18}$-alkyl polyglucosides. This combination of surfactants also achieves a particularly good cleaning effect without negatively influencing the hair volume achieved with the hydrophobic fumed silica or the long-lasting hold of the hair volume.

Furthermore, an additional particularly preferred embodiment of the inventive cosmetic agent is exemplified in that the at least one first surfactant (A) is selected from $C_{12}$-$C_{18}$-acyl sarcosinates and the at least one second surfactant (B) is selected from olefin sulfonates. This combination of surfactants also achieves a particularly good cleaning effect without negatively influencing the hair volume achieved with the hydrophobic fumed silica or the long-lasting hold of the hair volume.

Furthermore, an additional particularly preferred embodiment of the inventive cosmetic agent is exemplified in that the at least one first surfactant (A) is selected from $C_{16}$-alkyl trimethyl ammonium chloride or $C_{22}$-alkyl trimethyl ammonium chloride and the at least one second surfactant (B) is selected from N-[3-(dimethylamino)propyl]octadecanamide. This combination of surfactants achieves a particularly good conditioning effect without negatively influencing the hair volume achieved with the hydrophobic fumed silica or the long-lasting hold of the hair volume.

The at least one surfactant (A), particularly the aforementioned particularly preferred surfactant (A), is preferably contained in cosmetic agents as contemplated herein specific total amounts. As contemplated herein, it is therefore preferable for the at least one surfactant (A) to be contained in a total amount of from about 0.5 to about 25 wt. %, preferably from about 0.8 to about 22 wt. %, more preferably from about 1.0 to about 18 wt. %, particularly from about 1.5 to about 15 wt. % relative to the total weight of the cosmetic agent. If a mixture of different surfactants (A) is used, these quantity specifications relate to the total amount of the mixture of surfactants (A). The improved and long-lasting hair volume achieved with the at least one hydrophobic fumed silica, particularly the silica modified with hexamethyldisilazane can be further enhanced with the use of a surfactant (A), particularly the aforementioned special surfactants. Use of the aforementioned total amounts of surfactant (A) simultaneously achieve an outstanding cleaning and/or conditioning effect.

The at least one surfactant (B), particularly the aforementioned particularly preferred surfactant (B), is also preferably contained in cosmetic agents as contemplated herein specific total amounts. As contemplated herein, it is therefore preferable for the at least one second surfactant (B) to be contained in a total amount of from about 0.05 to about 15 wt. %, preferably from about 0.1 to about 10 wt. %, more preferably from about 0.2 to about 8.0 wt. %, particularly from about 0.3 to about 6.0 wt. % relative to the total weight of the cosmetic agent. If a mixture of different surfactants (B) is used, these quantity specifications relate to the total amount of the mixture of surfactants (B). The improved and long-lasting hair volume achieved with the at least one hydrophobic fumed silica, particularly the silica modified with hexamethyldisilazane can be further enhanced with the use of a surfactant (B), particularly the aforementioned special surfactants. Use of the aforementioned total amounts of surfactant (B) simultaneously achieve an outstanding cleaning and/or conditioning effect.

In addition to the previously mentioned mandatory components a) to c), the cosmetic agents according to this present disclosure contain additional ingredients.

The cosmetic agent preferably contains at least one additional surfactant (C), which is different from surfactants (A) and (B). In the context of the present disclosure, use of specific surfactants (C) has been found to be advantageous. As contemplated herein, therefore, it is preferably that the cosmetic agent contains at least one third surfactant (C) selected from the group of (i) cocamide monoethanolamine, (ii) alkyl ether carboxylic acids having 8 to 18 carbon atoms in the alkyl chain and (iii) combinations thereof. With use of these aforementioned surfactants (C), the cleaning and/or conditioning effect of the inventive cosmetic agents can be further enhanced.

In this context, it is advantageous if the at least one additional surfactant (C) is used in a specific total amount. Therefore, preferred cosmetic agents of the present disclosure are exemplified in that the at least one additional surfactant (C) is contained in a total amount of from about 0.01 to about 25 wt. %, preferably from about 0.05 to about 20 wt. %, more preferably from about 0.1 to about 18 wt. %, particularly from about 0.15 to about 15 wt. %, relative to the total weight of the cosmetic agent.

Furthermore, it has been found to be advantageous if the cosmetic agent as contemplated herein also contains at least one specific thickening agent in order to adjust the viscosity such that the agent can be easily removed from the packaging, but still has good distributability on the hair. Preferred embodiments of the inventive cosmetic agents, therefore, are exemplified in that they contain at least one methyl glucose ether having 110 to 130 ethylene oxide units which is esterified with oleic acid. Preferred used methyl glucose ethers are the compounds available under the INCI designation Glucamate DOE-120, which have the CAS no. 86893-19-8 and the following formula (VD-I):

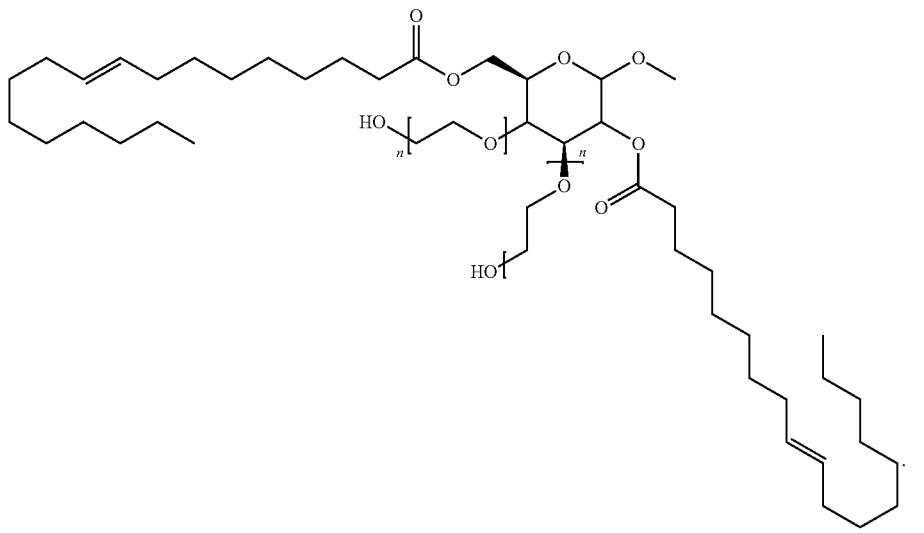

(VD-I)

In this context, it is preferred that the at least one thickening agent, particularly the thickening agent of formula (VD-I) is contained in a specific total amount. As contemplated herein, it is therefore advantageous for the at least one methyl glucose ester having 110 to 130 ethylene oxide units which is esterified with oleic acid to be contained in a total amount of from about 0.01 to about 3.0 wt. %, preferably from about 0.02 to about 2.0 wt. %, more preferably from about 0.03 to about 1.5 wt. %, particularly from about 0.05 to about 1.0 wt. % relative to the total weight of the cosmetic agent. Use of the thickening agent, particularly of compounds of formula (VD-I) achieves an adequate thickening of the cosmetic agent as contemplated herein. As a result, the inventive agent can be removed from the package easily and applied to the hair.

In addition to the aforementioned components, the cleaning compositions contain a series of further optional components. Preference is given to the addition of additional active ingredients having additional cosmetic care properties to the cleaning compositions in order to aid the conditioning of the skin and/or the hair. These ingredients are preferably selected from various surfactants (D) surfactants (A) to (C); (ii) oil components; (iii) cationic polymers; (iv) plant extracts; (v) protein hydrolysates; (vi) moisture retention agents; and (vii) mixtures thereof.

In the context of the present disclosure, it can be stipulated that the cosmetic agents contain at least one additional surfactant (D) which is different from surfactants (A) to (C). It is preferred that the additional surfactant (D) is selected from nonionic surfactants, particularly from adducts of 0 to 10 mol ethylene oxide on glyceryl monostearate and/or from adducts of 30 to 50 mol ethylene oxide on hydrated castor oil and/or from adducts of 3 to 5 mol ethylene oxide on alcohols having 10 to 14 carbon atoms. The surfactants (D) are used in the cosmetic agents as contemplated herein preferably in a total amount of from about 0.05 to about 2.5 wt. %, more preferably from about 0.1 to about 2.0 wt. %, even more preferably from about 0.2 to about 1.5 wt. %, particularly from about 0.3 to about 1.0 wt. %, relative to the total weight of the cosmetic agent.

Suitable oil components as contemplated herein can be selected from mineral, natural or synthetic oil components, such as petrolatum, paraffins, silicones, alcohols, fatty acid esters, natural oils of plant and animal origin and mixtures thereof. The oil components can be used in an amount of from about 0.005 to about 20 wt. %, preferably from about 0.01 to about 10 wt. %, more preferably from about 0.05 to about 5.0 wt. % and particularly from about 0.2 to about 3.0 wt. % relative to the total weight of the cosmetic agent.

The person skilled in the art understands silicones to mean various organic structures of organic silicone compounds which can be contained in the inventive cosmetic agents, preferably in a total amount of from about 0.01 to about 3.0 wt. %, more preferably from about 0.05 to about 2.0 wt. %, particularly from about 0.1 to about 1.0 wt. % relative to the total weight of the cosmetic agent.

Preference is given to silicones that are selected from at least one representative of the group of organic silicone compounds comprising (i) polyalkylsiloxanes, polyarylsiloxanes, polyalkylarylsiloxanes that are volatile or non-volatile, straight-chained, branched or cyclical, cross-linked or non-cross-linked; (ii) polysiloxanes with amine groups, thiol groups, carboxylate groups; hydroxylated groups, alkoxylated groups; acyloxyalkyl groups; amphoteric groups; bisulfate groups; hydroxy acyl amino groups; carboxy groups; sulfonic acid groups and sulfate- or thiosulfate groups; (iii) linear polysiloxane(A)-polyoxyalkylene(B)-block copolymers of type (A-B)n having n>3; (iv) grafted silicone polymers having a non-silicone-containing organic backbone including a main chain in which least one polysiloxane macromer is formed from organic monomers which do not contain silicone onto which the at least one polysiloxane macromer was grafted in the chain and, optionally, on a chain end; (v) grafted silicone polymers having a polyxiloxane backbone onto which non-silicone-containing organic monomers were grafted which have a polysiloxane main chain onto which at least one organic macromer which does not contain silicone was grafted in the chain and, optionally, on at least one of its end; and (vi) or mixtures thereof.

In an embodiment of the present disclosure, the conditioning agent is a conditioning silicone having a viscosity of from about 20,000 to about 120,000 mPas, with particular preference being given to from about 40,000 to about 80,000 mPas.

Particular preference is given to at least one oil component selected from silicones, particularly dimethicones, amodimethicones or dimethiconoles.

Saturated, mono- or poly-unsaturated, branched or unbranched fatty alcohols with $C_6$-$C_{30}$-, preferably $C_{10}$-$C_{22}$ and most preferably $C_{12}$-$C_{22}$ carbon atoms, can be used as fatty alcohols. Decanol, octanol, octenol, dodecenol, decenol, octadienol, dodecadienol, decadienol, oleylalcohol, erucaalcohol, ricinolalcohol, stearylalcohol, isostearylalcohol, cetylalcohol, laurylalcohol, myristylalcohol, arachidylalcohol, caprylalcohol, caprinalcohol, linoleylalcohol, linolenylalcohol and behenylalcohol, as well as the guerbetalcohols thereof, can be used in the context of the present disclosure. This list contains purely examples and is not exhaustive. The fatty alcohols preferably originate, however, from natural fatty acids having $C_6$-$C_3$O-carbon atoms, wherein the recovery from the esters of fatty acids by employing reduction can normally be assumed. As contemplated herein, fatty alcohol fractions produced by reducing naturally-occurring triglycerides such as beef tallow, palm oil, peanut oil, rapeseed oil, cotton seed oil, soya oil, sunflower oil and linseed oil, or the fatty acid esters produced from the trans-esterification products with corresponding alcohols can also be used. These substances therefore constitute a mixture of different fatty alcohols. Such substances are commercially available, for example under the namesStenol®, i.e. Stenol® 1618 orLanette®, i.e. Lanette® 0 or Lorol®, i.e. Lorol® C8, Lorol® C14, Lorol® C18, Lorol® C8-18, HD-Ocenol, Crodacol®, i.e. Crodacol® CS, Novol, Eutanol® G, Guerbitol® 16, Guerbitol® 18, Guerbitol® 20, Isofol® 12, Isofol® 16, Isofol® 24, Isofol® 36, Isocarb® 12, Isocarb® 16 or Isocarb® 24. As contemplated herein, wool wax alcohols, such as those commercially available under the trade names of Corona®, White Swan®, Coronet® or Fluilan®, can also be used.

Suitable fatty alcohols as contemplated herein are preferably used in the cosmetic agents in a total amount of from about 0.01 to about 3.0 wt. %, more preferably from about 0.05 to about 2.0 wt. %, particularly from about 0.1 to about 1.0 wt. % relative to the total weight of the cosmetic agent.

Solid paraffins or iso-paraffins, carnauba waxes, beeswaxes, candelilla waxes, ozokerites, ceresine, spermaceti, sunflower wax, fruit wax, such as apple wax or citrus wax, micro-waxes from PE- or PP can be used as natural or synthetic waxes as contemplated herein.

The natural and synthetic cosmetic oil bodies include, for example:
- liquid paraffin oils, isoparaffin oils and synthetic hydrocarbons, as well as Di-n-alkyl ethers having a total of 12 to 36 carbon atoms, particularly 12 to 24 carbon atoms,
- Ester oils. Ester oils include the esters from $C_6$-$C_{30}$ fatty acids with $C_2$-$C_{30}$-alcohols. Preference is given to mono esters of fatty acids with alcohols with 2 to 24 carbon atoms,
- dicarboxylic acid esters,
- symmetrical, asymmetrical or cyclical esters of carbonic acids with fatty alcohols, glycerin carbonate or dicaprylylcarbonate,
- trifatty acid esters of saturated and/or unsaturated linear and/or branched fatty acids with glycerin,
- fatty acid partial glycerides of the formula,

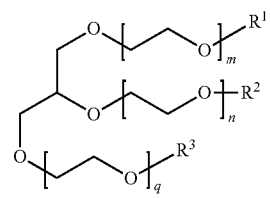

wherein $R^1$, $R^2$ and $R^3$ independently of each other denote hydrogen or a linear or branched, saturated and/or unsaturated acyl radical having 6 to 22, preferably 12 to 18 carbon atoms with the condition that at least one of these groups denotes an acyl radical and at least one of these groups denotes hydrogen. The sum (m+n+q) denotes 0 or integers from 1 to 100, preferably 0 or 5 to 25.

In a particularly preferred embodiment of the present disclosure, a plant oil is used as an oil component.

Natural oils include, in particular, amaranthus seed oil, apricot kernel oil, arganil, avocado oil, babassu oil, cottonseed oil, borage seed oil, cameline oil, safflower oil, peanut oil, pomegranate core oil, grapefruit seed oil, hemp oil, hazelnut oil, palm seed oil, jojoba oil, linseed oil, macadamia nut oil, corn oil, almond oil, manila oil, evening primrose oil, olive oil, palm oil, palm kernel oil, parannut oil, pecknut oil, peach kernel oil, rapeseed oil, castor oil, sandalwood oil, castor oil, sesame oil, soya oil, sunflower oil, grapeseed oil, walnut oil and wild-type oil.

As contemplated herein, particular preference is given to avocado oil, apricot kernel oil, hemp oil, jojoba oil, cocoa butter, almond oil, olive oil, peach kernel oil, shea butter, sunflower oil and grapeseed oil.

The aforementioned oils and/or mixtures thereof are preferably used in the inventive cosmetic agents in a total amount of from about 0.01 to about 3.0 wt. %, more preferably from about 0.05 to about 2.5 wt. %, particularly from about 0.1 to about 2.0 wt. % relative to the total weight of the cosmetic agent.

Additional conditioning components as contemplated herein include cationic polymers. Suitable cationic polymers as contemplated herein are understood to mean polymers having "temporarily cationic" or "permanently cationic" groups in the main and/or side chain. As contemplated herein, the term "permanently cationic" is understood to mean polymers which have at least one cationic group independently of the pH value of the agent. These are normally polymers which contain a quaternary nitrogen atom, i.e. in the form of an ammonium group.

In particular, polymers in which the quaternary ammonium group has a $C_{1-4}$-hydrocarbon group on a polymer main chain produced from acrylic acid, methacrylic acid or derivatives thereof have been found to be particularly suitable.

Particularly preferred cationic polymers are homopolymers of the general formula

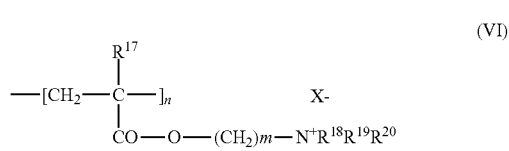

(VI)

where $R^{17}$=—H or —$CH_3$, $R^{18}$, $R^{19}$ and $R^{20}$ are selected independently of each other from $C_{1-4}$-alkyl-, -alkenyl- or -hydroxyalkyl groups, m 1, 2, 3 or 4, n denotes a natural number and X denotes a physiologically compatible organic or inorganic anion, as well as copolymers including the monomer units and nonionogenic monomer units in formula (VI).

In the context of the aforementioned polymers as contemplated herein, preference is given to polymers which meet at least one of the following conditions:
$R^{17}$ denotes a methyl group
$R^{18}$, $R^{19}$ and $R^{20}$ denote methyl groups
m has the value 2.

For example, halogenide ions, sulfate ions, phosphate ions, methosulfate ions and organic ions such as lactate-, citrate-, tartrate- and acetate ions are considered physiologically compatible $X^-$ counter-ions. Preference is given to halogenide ions, particularly chloride. As contemplated herein, suitable homo- or copolymers which are derived from formula (VI) are the cationic polymers commercially available, for example, under the trade names Salcare® SC 95, Salcare® SC 96 and Salcare® SC 92.

Other preferred cationic polymers include
quaternated cellulose derivatives, such as those commercially available under the names Celquat® and Polymer JR®, The compounds Celquat® H 100, Celquat® L 200 and polymer JR®400 are preferred quaternated cellulose derivatives,
hydrophobically modified cellulose derivatives, such as the cationic polymers sold under the trade name Soft-Cat®,
cationic alkylpolyglycosides,
cationized honey, the commercial product Honeyquat® 50, for example,
cationic guar derivatives, such as the products sold under the trade names Cosmedia® Guar and Jaguar®, in particular,
polysiloxans with quaternary groups,
polymeric dimethyldiallyl ammonium salts and the copolymers thereof having esters and amides of acrylic acid and methacrylic acid,
copolymers of vinylpyrrolidone with quaternated derivatives of dialkylaminoalkylacrylate and -methacrylate,
vinylpyrrolidone-vinylimidazoliummethochloride-copolymers,
quaternated polyvinyl alcohol, and the polymers known by the names
Polyquaternium 2,
Polyquaternium 17,
Polyquaternium 18 and
Polyquaternium 27 having nitrogen atoms in the polymer main chain.

The polymers known under the names Polyquaternium-24 (commercial product, e.g. Quatrisoft® LM 200) can also be used as cationic polymers. The copolymers of vinylpyrrolidone, such as those commercially available as Copolymer 845 (manufacturer: ISP), Gaffix® VC 713 (manufacturer: ISP), Gafquat®ASCP 1011, Gafquat®HS 110, Luviquat® 8155 and Luviquat® MS 370 can also be used as contemplated herein.

Further cationic polymers as contemplated herein are the so-called "temporarily cationic" polymers. These polymers normally contain an amino group which is present with specific pH values as a quaternary ammonium group and, therefore, is cationic. Preference is given, for example, to chitosane and derivatives thereof, which are commercially available under the trade names Hydagen® CMF, Hydagen® HCMF, Kytamer® PC and Chitolam® NB/101. Chitosanes are diacetylated chitines which are available in different deacetylization degrees and different degrees of decomposition (molecular weights).

In a particularly preferred embodiment of the present disclosure, the inventive cosmetic agents contain at least one cationic polymer which is selected from the group of cationic homopolymers of 2-methacryloxyethyltrimethyl ammonium chloride (Polyquaternium-37) and/or quaternated hydroxyethyl cellulose (Polyquaternium-10).

The at least one cationic polymer is preferably contained in the cosmetic agent as contemplated herein in a total amount of from about 0.1 to about 5.0 wt. %, more preferably from about 0.2 to about 3.0 wt. %, particularly from about 0.5 to about 2.0 wt. % relative to the total weight of the cosmetic agent. Use of the aforementioned particularly preferred cationic polymers, particularly of Polyquaternium-37 and/or Polyquaternium-10, in the aforementioned total amounts achieves an improvement of the conditioning effect of the cosmetic agents as contemplated herein.

As contemplated herein, suitable plant extracts include extracts which can be produced from all parts of a plant. Normally, these extracts are produced by employing extraction of the entire plant. However, in individual cases, preference can be given to extracts produced exclusively from blossom and/or leaves of plants.

As contemplated herein, particular preference is given to the extracts from green tea, white tea, oak bark, stinging nettles, hamamelis, hops, camomile, burdock root, horsetail, white mandrel, linden blossoms, litski, almond, aloe vera, pine needle, horse chestnut, sandalwood, juniper, coconut, mango, apricot, lemon, wheat, kiwi, melon, orange, grapefruit, sage, rosemary, birch, malve, wiesbaden, quidel, yarrow, thyme, melissa, hautharrow, huflatticch, ebisch, ginseng, ginger root, Echinacea purpurea, Olea europa, Foeniculus vulgaris and Apim graveolens.

Water, alcohols and mixtures thereof can be used as extraction agents for production of the aforementioned plant extracts. Alcohols are preferably understood to mean lower alcohols, such as ethanol and isopropanol, particularly multivalent alcohols, such as ethylene glycol and propylene glycol as sole extraction agents and in combination with water. Water/propylene-glycol-based plant extracts in a ratio of from about 1:10 to about 10:1 have been found to be particularly suitable.

As contemplated herein, the plant extracts can be used in pure or diluted form. If they are used in diluted form, they normally contain from about 2.0 to about 80 wt. % active substance and the extraction agent or extraction agent mixture used in their production as a solvent.

In a further embodiment of the present disclosure, the inventive cosmetic agents can also contain protein hydrolysates and/or derivatives thereof to further enhance their skin- and hair-nurturing effect. Protein hydrolysates are product mixtures obtained through the acidically, basically or enzymatically catalyzed decomposition of proteins. As contemplated herein, protein hydrolysates of plant and animal origin can be used.

Animal protein hydrolysates are, for example, elastine-, collagen-, keratin-, seiden- and milk-protein-hydrolysates, which can also be present in the form of salts. Such products are sold, for example, under the trade names Dehylan® (Cognis), Promois® (Interorgana), Collapuron® (Cognis), Nutrilan® (Cognis), Gelita-Sol® (Deutsche Gelatine Fabriken Stoess & Co), Lexein® (Inolex) and Kerasol® (Croda).

As contemplated herein, preference is given to protein hydrolysates of plant original, such as soya-, almond-, rice-, pea-, potato- and wheat protein hydrolysates. Such products are available, for example, under the trade names Gluadin® (Cognis), DiaMin® (Diamalt), Lexein® (Inolex) and Crotein® (Croda).

Although use of protein hydrolysates as such is preferred, amino acid mixtures obtained in another manner or individual amino acids, such as arginine, lysine, histidine or pyrroglutamic acid also be optionally used instead. Use of derivatives of protein hydrolysates, for example, in the form of their fatty acid condensation products, is also possible. Such protect are sold, for example, under the names Lamepon® (Cognis), Gluadin® (Cognis), Lexein® (Inolex), Crolastin® (Croda) or Crotein® (Croda).

As contemplated herein, cationized protein hydrolysates can also be used wherein the basic protein hydrolysate originates from an animal, such as collagen, milk or keratin, from a plant, such as from wheat, corn, rice, potatoes, soya or almonds, from marine life forms, such as from fish collagen or algae, or from biotechnologically obtained protein hydrolysates. The protein hydrolysates on which the cationic derivatives as contemplated herein are based can be obtained from the appropriate proteins by employing a chemical, particularly alkaline or acidic hydrolysis, enzymatic hydrolysis and/or with a combination of the two types of hydrolysis. The hydrolysis of proteins normally produces a protein hydrolysate having a molecular weight distribution from about 100 Dalton to several thousand Dalton. Preference is given to cationic protein hydrolysates having a basic protein portion with a molecular weight from about 100 to about 25,000 Dalton, preferably from about 250 to about 5,000 Dalton. Furthermore, cationic protein hydrolysates are understood to mean quaternated amino acids and mixtures thereof. Quaternization of protein hydrolysates or amino acids is frequently carried out by employing quaternary ammonium salts, such as N,N-dimethyl-N-(n-alkyl-)-N-(2-hydroxy-3-chloro-n-propyl)-ammonium halogenides. Furthermore, the cationic protein hydrolysates can be derivatized even further. Typical examples for cationic protein hydrolysates and derivatives thereof, which can be used as contemplated herein, include, for example, Cocodimonium Hydroxypropyl Hydrolyzed Collagen, Cocodimonium Hydroxypropyl Hydrolyzed Casein, Cocodimonium Hydroxypropyl Hydrolyzed Collagen, Cocodimonium Hydroxypropyl Hydrolyzed Hair Keratin, Cocodimonium Hydroxypropyl Hydrolyzed Keratin, Cocodimonium Hydroxypropyl Hydrolyzed Rice Protein, Cocodimonium Hydroxypropyl Hydrolyzed Silk, Cocodimonium Hydroxypropyl Hydrolyzed Soy Protein, Cocodimonium Hydroxypropyl Hydrolyzed Wheat Protein, Cocodimonium Hydroxypropyl Silk Amino Acids, Hydroxypropyl Arginine Lauryl/Myristyl Ether HCl, Hydroxypropyltrimonium Gelatin, Hydroxypropyltrimonium Hydrolyzed Casein, Hydroxypropyltrimonium Hydrolyzed Collagen, Hydroxypropyltrimonium Hydrolyzed Conchiolin Protein, Hydroxypropyltrimonium Hydrolyzed keratin, Hydroxypropyltrimonium Hydrolyzed Rice Bran Protein, Hydroxyproypltrimonium Hydrolyzed Silk, Hydroxypropyltrimonium Hydrolyzed Soy Protein, Hydroxypropyl Hydrolyzed Vegetable Protein, Hydroxypropyltrimonium Hydrolyzed Wheat Protein, Hydroxypropyltrimonium Hydrolyzed Wheat Protein/Siloxysilicate, Laurdimonium Hydroxypropyl Hydrolyzed Soy Protein, Laurdimonium Hydroxypropyl Hydrolyzed Wheat Protein, Laurdimonium Hydroxypropyl Hydrolyzed Wheat Protein/Siloxysilicate, Lauryldimonium Hydroxypropyl Hydrolyzed Casein, Lauryldimonium Hydroxypropyl Hydrolyzed Collagen, Lauryldimonium Hydroxypropyl Hydrolyzed Keratin, Lauryldimonium Hydroxypropyl Hydrolyzed Silk, Lauryldimonium Hydroxypropyl Hydrolyzed Soy Protein, Steardimonium Hydroxypropyl Hydrolyzed Casein, Steardimonium Hydroxypropyl Hydrolyzed Collagen, Steardimonium Hydroxypropyl Hydrolyzed Keratin, Steardimonium Hydroxypropyl Hydrolyzed Rice Protein, Steardimonium Hydroxypropyl Hydrolyzed Silk, Steardimonium Hydroxypropyl Hydrolyzed Soy Protein, Steardimonium Hydroxypropyl Hydrolyzed Vegetable Protein, Steardimonium Hydroxypropyl Hydrolyzed Wheat Protein, Steartrimonium Hydroxyethyl Hydrolyzed Collagen, Quaternium-76 Hydrolyzed Collagen, Quaternium-79 Hydrolyzed Collagen, Quaternium-79 Hydrolyzed Keratin, Quaternium-79 Hydrolyzed Milk Protein, Quaternium-79 Hydrolyzed Silk, Quaternium-79 Hydrolyzed Soy Protein and Quaternium-79 Hydrolyzed Wheat Protein. Particular preference is given to plant-based cationic protein hydrolysates and derivatives thereof, particularly hydrolysated keratin.

The at least one protein hydrolysate and/or derivatives thereof, particularly hydrolyzated keratin, are preferably used in a total amount of from about 0.01 to about 10 wt. %, more preferably from about 0.1 to about 5.0 wt. %, particularly from about 0.1 to about 3.0 wt. % relative to the total weight of the cosmetic agent.

Furthermore, it can be advantageous to add moisture-retaining agents and/or penetration excipients and/or expanding agents to the inventive cosmetic agents. These excipients assure better penetration of active ingredients into the keratinous fibers or help the keratinous fibers to expand. This includes, for example, urea and urea derivatives, guanidine and derivatives thereof, arginine and derivatives thereof, water glass, imidazole and derivatives thereof, histidine and derivatives thereof, benzyl alcohol, glycerol, glycol and glycol ethers, propylene glycol and propylene glycol ethers, for example propylene glycol monoethyl ether, carbonates, hydrogen carbonates, diols and triols, and in particular 1,2-diols and 1,3-diols such as, for example, 1,2-propanediol, 1,2-pentanediol, 1,2-hexanediol, 1,2-dodecanediol, 1,3-propanediol, 1,6-hexanediol, 1,5-pentanediol, 1,4-butanediol. As contemplated herein, glycerin is particularly well-suited.

The moisture-retaining agents are preferably used in the inventive cosmetic agents in a total amount of from about 0.01 to about 10 wt. %, more preferably from about 0.05 to about 5.0 wt. %, particularly from about 0.1 to about 3.0 wt. % relative to the total weight of the cosmetic agent.

The following tables list particularly preferred embodiments of AF 1 to AF 72 of the cosmetic agent as contemplated herein (all figures in wt. %).

|  | AF 1 | AF 2 | AF 3 | AF 4 |
| --- | --- | --- | --- | --- |
| Hydrophobic fumed silica | 0.01 to 5.0 | 0.1 to 4.0 | 0.3 to 2.0 | 0.5 to 1.0 |
| Surfactant (A) [1)] | 0.5 to 25 | 0.8 to 22 | 1.0 to 18 | 1.5 to 15 |
| Surfactant (B) [2)] | 0.05 to 15 | 0.1 to 10 | 0.2 to 8.0 | 0.3 to 6.0 |
| Cosmetic carrier | ad 100 | ad 100 | ad 100 | ad 100 |

|  | AF 5 | AF 6 | AF 7 | AF 8 |
|---|---|---|---|---|
| Hydrophobic fumed silica [3] | 0.01 to 5.0 | 0.1 to 4.0 | 0.3 to 2.0 | 0.5 to 1.0 |
| Surfactant (A) [1] | 0.5 to 25 | 0.8 to 22 | 1.0 to 18 | 1.5 to 15 |
| Surfactant (B) [2] | 0.05 to 15 | 0.1 to 10 | 0.2 to 8.0 | 0.3 to 6.0 |
| Cosmetic carrier | ad 100 | ad 100 | ad 100 | ad 100 |

|  | AF 9 | AF 10 | AF 11 | AF 12 |
|---|---|---|---|---|
| Hydrophobic fumed silica [4] | 0.01 to 5.0 | 0.1 to 4.0 | 0.3 to 2.0 | 0.5 to 1.0 |
| Surfactant (A) [1] | 0.5 to 25 | 0.8 to 22 | 1.0 to 18 | 1.5 to 15 |
| Surfactant (B) [2] | 0.05 to 15 | 0.1 to 10 | 0.2 to 8.0 | 0.3 to 6.0 |
| Cosmetic carrier | ad 100 | ad 100 | ad 100 | ad 100 |

|  | AF 13 | AF 14 | AF 15 | AF 16 |
|---|---|---|---|---|
| Hydrophobic fumed silica [5] | 0.01 to 5.0 | 0.1 to 4.0 | 0.3 to 2.0 | 0.5 to 1.0 |
| Surfactant (A) [1] | 0.5 to 25 | 0.8 to 22 | 1.0 to 18 | 1.5 to 15 |
| Surfactant (B) [2] | 0.05 to 15 | 0.1 to 10 | 0.2 to 8.0 | 0.3 to 6.0 |
| Cosmetic carrier | ad 100 | ad 100 | ad 100 | ad 100 |

|  | AF 17 | AF 18 | AF 19 | AF 20 |
|---|---|---|---|---|
| Hydrophobic fumed silica [3] | 0.01 to 5.0 | 0.1 to 4.0 | 0.3 to 2.0 | 0.5 to 1.0 |
| Surfactant (A) [6] | 0.5 to 25 | 0.8 to 22 | 1.0 to 18 | 1.5 to 15 |
| Surfactant (B) [7] | 0.05 to 15 | 0.1 to 10 | 0.2 to 8.0 | 0.3 to 6.0 |
| Cosmetic carrier | ad 100 | ad 100 | ad 100 | ad 100 |

|  | AF 21 | AF 22 | AF 23 | AF 24 |
|---|---|---|---|---|
| Hydrophobic fumed silica [3] | 0.01 to 5.0 | 0.1 to 4.0 | 0.3 to 2.0 | 0.5 to 1.0 |
| Surfactant (A) [8] | 0.5 to 25 | 0.8 to 22 | 1.0 to 18 | 1.5 to 15 |
| Surfactant (B) [9] | 0.05 to 15 | 0.1 to 10 | 0.2 to 8.0 | 0.3 to 6.0 |
| Cosmetic carrier | ad 100 | ad 100 | ad 100 | ad 100 |

|  | AF 25 | AF 26 | AF 27 | AF 28 |
|---|---|---|---|---|
| Hydrophobic fumed silica [3] | 0.01 to 5.0 | 0.1 to 4.0 | 0.3 to 2.0 | 0.5 to 1.0 |
| Surfactant (A) [10] | 0.5 to 25 | 0.8 to 22 | 1.0 to 18 | 1.5 to 15 |
| Surfactant (B) [11] | 0.05 to 15 | 0.1 to 10 | 0.2 to 8.0 | 0.3 to 6.0 |
| Cosmetic carrier | ad 100 | ad 100 | ad 100 | ad 100 |

|  | AF 29 | AF 30 | AF 31 | AF 32 |
|---|---|---|---|---|
| Hydrophobic fumed silica [3] | 0.01 to 5.0 | 0.1 to 4.0 | 0.3 to 2.0 | 0.5 to 1.0 |
| Surfactant (A) [12] | 0.5 to 25 | 0.8 to 22 | 1.0 to 18 | 1.5 to 15 |
| Surfactant (B) [13] | 0.05 to 15 | 0.1 to 10 | 0.2 to 8.0 | 0.3 to 6.0 |
| Cosmetic carrier | ad 100 | ad 100 | ad 100 | ad 100 |

|  | AF 33 | AF 34 | AF 35 | AF 36 |
|---|---|---|---|---|
| Hydrophobic fumed silica [3] | 0.01 to 5.0 | 0.1 to 4.0 | 0.3 to 2.0 | 0.5 to 1.0 |
| Surfactant (A) [14] | 0.5 to 25 | 0.8 to 22 | 1.0 to 18 | 1.5 to 15 |
| Surfactant (B) [15] | 0.05 to 15 | 0.1 to 10 | 0.2 to 8.0 | 0.3 to 6.0 |
| Cosmetic carrier | ad 100 | ad 100 | ad 100 | ad 100 |

|  | AF 37 | AF 38 | AF 39 | AF 40 |
|---|---|---|---|---|
| Hydrophobic fumed silica [3] | 0.01 to 5.0 | 0.1 to 4.0 | 0.3 to 2.0 | 0.5 to 1.0 |
| Surfactant (A) [10] | 0.5 to 25 | 0.8 to 22 | 1.0 to 18 | 1.5 to 15 |
| Surfactant (B) [11] | 0.05 to 15 | 0.1 to 10 | 0.2 to 8.0 | 0.3 to 6.0 |
| Surfactant (C) [16] | 0.01 to 25 | 0.05 to 20 | 0.1 to 18 | 0.15 to 15 |
| Cosmetic carrier | ad 100 | ad 100 | ad 100 | ad 100 |

|  | AF 41 | AF 42 | AF 43 | AF 44 |
|---|---|---|---|---|
| Hydrophobic fumed silica [3] | 0.01 to 5.0 | 0.1 to 4.0 | 0.3 to 2.0 | 0.5 to 1.0 |
| Surfactant (A) [6] | 0.5 to 25 | 0.8 to 22 | 1.0 to 18 | 1.5 to 15 |
| Surfactant (B) [7] | 0.05 to 15 | 0.1 to 10 | 0.2 to 8.0 | 0.3 to 6.0 |
| Surfactant (C) [17] | 0.01 to 25 | 0.05 to 20 | 0.1 to 18 | 0.15 to 15 |
| Cosmetic carrier | ad 100 | ad 100 | ad 100 | ad 100 |

|  | AF 45 | AF 46 | AF 47 | AF 48 |
|---|---|---|---|---|
| Hydrophobic fumed silica [3] | 0.01 to 5.0 | 0.1 to 4.0 | 0.3 to 2.0 | 0.5 to 1.0 |
| Surfactant (A) [8] | 0.5 to 25 | 0.8 to 22 | 1.0 to 18 | 1.5 to 15 |
| Surfactant (B) [9] | 0.05 to 15 | 0.1 to 10 | 0.2 to 8.0 | 0.3 to 6.0 |

| | | | | |
|---|---|---|---|---|
| Surfactant (C) [17] | 0.01 to 25 | 0.05 to 20 | 0.1 to 18 | 0.15 to 15 |
| Cosmetic carrier | ad 100 | ad 100 | ad 100 | ad 100 |

| | AF 49 | AF 50 | AF 51 | AF 52 |
|---|---|---|---|---|
| Hydrophobic fumed silica [3] | 0.01 to 5.0 | 0.1 to 4.0 | 0.3 to 2.0 | 0.5 to 1.0 |
| Surfactant (A) [10] | 0.5 to 25 | 0.8 to 22 | 1.0 to 18 | 1.5 to 15 |
| Surfactant (B) [11] | 0.05 to 15 | 0.1 to 10 | 0.2 to 8.0 | 0.3 to 6.0 |
| Surfactant (C) [17] | 0.01 to 25 | 0.05 to 20 | 0.1 to 18 | 0.15 to 15 |
| Cosmetic carrier | ad 100 | ad 100 | ad 100 | ad 100 |

| | AF 53 | AF 54 | AF 55 | AF 56 |
|---|---|---|---|---|
| Hydrophobic fumed silica [3] | 0.01 to 5.0 | 0.1 to 4.0 | 0.3 to 2.0 | 0.5 to 1.0 |
| Surfactant (A) [12] | 0.5 to 25 | 0.8 to 22 | 1.0 to 18 | 1.5 to 15 |
| Surfactant (B) [13] | 0.05 to 15 | 0.1 to 10 | 0.2 to 8.0 | 0.3 to 6.0 |
| Surfactant (C) [17] | 0.01 to 25 | 0.05 to 20 | 0.1 to 18 | 0.15 to 15 |
| Cosmetic carrier | ad 100 | ad 100 | ad 100 | ad 100 |

| | AF 57 | AF 58 | AF 59 | AF 60 |
|---|---|---|---|---|
| Hydrophobic fumed silica [3] | 0.01 to 5.0 | 0.1 to 4.0 | 0.3 to 2.0 | 0.5 to 1.0 |
| Surfactant (A) [6] | 0.5 to 25 | 0.8 to 22 | 1.0 to 18 | 1.5 to 15 |
| Surfactant (B) [7] | 0.05 to 15 | 0.1 to 10 | 0.2 to 8.0 | 0.3 to 6.0 |
| Methylglucose ether [18] | 0.01 to 3.0 | 0.02 to 2.0 | 0.03 to 1.5 | 0.05 to 1.0 |
| Cosmetic carrier | ad 100 | ad 100 | ad 100 | ad 100 |

| | AF 61 | AF 62 | AF 63 | AF 64 |
|---|---|---|---|---|
| Hydrophobic fumed silica [3] | 0.01 to 5.0 | 0.1 to 4.0 | 0.3 to 2.0 | 0.5 to 1.0 |
| Surfactant (A) [8] | 0.5 to 25 | 0.8 to 22 | 1.0 to 18 | 1.5 to 15 |
| Surfactant (B) [9] | 0.05 to 15 | 0.1 to 10 | 0.2 to 8.0 | 0.3 to 6.0 |
| Methylglucose ether [18] | 0.01 to 3.0 | 0.02 to 2.0 | 0.03 to 1.5 | 0.05 to 1.0 |
| Cosmetic carrier | ad 100 | ad 100 | ad 100 | ad 100 |

| | AF 65 | AF 66 | AF 67 | AF 68 |
|---|---|---|---|---|
| Hydrophobic fumed silica [3] | 0.01 to 5.0 | 0.1 to 4.0 | 0.3 to 2.0 | 0.5 to 1.0 |
| Surfactant (A) [10] | 0.5 to 25 | 0.8 to 22 | 1.0 to 18 | 1.5 to 15 |
| Surfactant (B) [11] | 0.05 to 15 | 0.1 to 10 | 0.2 to 8.0 | 0.3 to 6.0 |
| Methylglucose ether [18] | 0.01 to 3.0 | 0.02 to 2.0 | 0.03 to 1.5 | 0.05 to 1.0 |
| Cosmetic carrier | ad 100 | ad 100 | ad 100 | ad 100 |

| | AF 69 | AF 70 | AF 71 | AF 72 |
|---|---|---|---|---|
| Hydrophobic fumed silica [3] | 0.01 to 5.0 | 0.1 to 4.0 | 0.3 to 2.0 | 0.5 to 1.0 |
| Surfactant (A) [12] | 0.5 to 25 | 0.8 to 22 | 1.0 to 18 | 1.5 to 15 |
| Surfactant (B) [13] | 0.05 to 15 | 0.1 to 10 | 0.2 to 8.0 | 0.3 to 6.0 |
| Methylglucose ether [18] | 0.01 to 3.0 | 0.02 to 2.0 | 0.03 to 1.5 | 0.05 to 1.0 |
| Cosmetic carrier | ad 100 | ad 100 | ad 100 | ad 100 |

[1] selected from the group of (i) alkyl(ether)sulfates having 8 to 18 carbon atoms in the alkyl chain and 1 to 6 ethylene oxide units, (ii) $C_{12}$-$C_{18}$-acyl isethionates, (iii) $C_{12}$-$C_{18}$-acyl sarcosinates, (iv) $C_{10}$-$C_{22}$-alkyl trimethylammonium chlorides and (v) mixtures thereof and

[2] selected from the group of (i) $C_{8-18}$-alkyl amido-($C_{1-4}$-alkyl)betaines, (ii) $C_{10}$-$C_{18}$-alkyl amphoacetates and -diacetates, (iii) $C_{10}$-$C_{18}$-alkyl polyglucosides, (iv) N-[3-dimethylamino-($C_{1-4}$-alkyl)]-$C_{12-18}$-alkanamides, (v) $C_{12}$-$C_{18}$-olefin sulfonates and (vi) mixtures thereof.

[3] modified with hexamethyldisilazane,

[4] hydrophobic fumed silica modified with hexamethyldisilazane having a specific surface (BET) of from about 190 to about 250 m²/g,

[5] hydrophobic fumed silica modified with hexamethyldisilazane having a specific surface (BET) of form about 190 to about 250 m²/g and a tamp density of from about 50 to about 70 g/l,

[6] sodium lauryl(ether)sulfate having 2 to 4 ethylene oxide units,

[7] $C_{8-18}$-alkylamidopropylbetaine and/or disodium-$C_{10}$-$C_{18}$-alkylamphodiacetate,

[8] sodium tridecyl(ether)sulfate having 2 to 4 ethylene oxide units,

[9] $C_{12}$-alkylamphoacetate,

[10] $C_{12}$-$C_{18}$-acyl isethionate,

[11] $C_{10}$-$C_{18}$-alkylpolyglucoside,

[12] $C_{12}$-$C_{18}$-acyl sarcosinate,

[13] olefin sulfonate,

[14] $C_{16}$-alkyltrimethyl ammonium chloride or $C_{22}$-alkyltrimethyl ammonium chloride,

[15] N-[3-(dimethylamino)propyl]octadecanamide,

[16] alkylethercarboxylic acids having 8 to 18 carbon atoms in the alkyl chain,

[17] cocamide monoethanolamine,

[18] methylglucose ether with 110 to 130 ethylene oxide units, which is esterified with oleic acid.

The aforementioned embodiments AF 1 to AF 72 of the inventive cosmetic agents achieve a higher and longer-lasting hair volume with use of a hydrophobic fumed silica in comparison with agents without the hydrophobically modified fumed silica. However, the cleaning and/or conditioning effect and the texture of these agents is not negatively influenced with use of these silica. Therefore, the agents of embodiments AF 1 to AF 72 have outstanding cleaning and/or conditioning properties.

A second subject of the present disclosure is the use of at least one hydrophobic fumed silica in cosmetic agents for cleaning and/or conditioning of hair to increase the hair volume and/or improve lasting hold of the hair volume.

The statements about the inventive cosmetic agents apply mutatis mutandis with regard to the pyrogenic silica and further preferred embodiments.

The following examples explain the present disclosure without limiting it:

EXAMPLES

The hydrophobic silica used in the following examples is preferably a silica modified with mexamethyldisilazane having a specific surface (BET) of from about 190 to about 250 $m^2/g$.

Conditioning Cosmetic Agent (Specifications in Wt. %):

| Raw material | Quantity (wt. %) |
| --- | --- |
| Surfactant (A) [1] | 1.8 |
| Surfactant (B) [2] | 0.4 |
| Hydrophobic fumed silica | 1.0 |
| Cetearyl alcohol | 3.0 |
| Cutina GMS-V [3] | 0.3 |
| Isopropyl myristate | 0.8 |
| Citric acid | 0.5 |
| Sodium methylparaben | 0.3 |
| Cosmedia Triple C [4] | 0.4 |
| Nutrilan Keratin W PP [5] | 0.2 |
| Glycine | 0.1 |
| D-Panthenol 75% | 0.2 |
| Glycerin 99.5% | 0.2 |
| Isopropanol | 0.4 |
| Perfume | 0.35 |
| Water | Ad 100 |

[1] preferably selected from $C_{10}$-$C_{22}$-alkyltrimethyl ammonium chlorides, particularly mechatronics chloride,
[2] preferably selected from N-[3-dimethylamino-(C1-4-alkyl)]-C12-18-alkanamides, particularly N-[3-(dimethylamino)propyl]octadecanamide,
[3] INCI: Glyceryl stearate (BASF),
[4] INCI: Polyquaternium-37, Dicaprylyl Carbonate, Lauryl Glucoside (BASF),
[5] INCI: Hydrolyzed Keratin, from about 20-about 23 wt. % in water (BASF)

Cleaning Cosmetic Agent (Specifications in Wt. %):

| Raw material | Quantity (wt. %) |
| --- | --- |
| Surfactant (A) [1] | 8.7 |
| Surfactant (B) [2] | 6.0 |
| Hydrophobic fumed silica | 1.0 |
| Sodium hydroxide 50% | 0.11 |
| Citric acid | 0.4 |
| Sodium benzoate | 0.50 |
| D-Panthenol 75% | 0.20 |
| Euperlan PK 3000 AM [3] | 2.0 |
| Glycine | 0.20 |
| Nutrilan Keratin W PP [4] | 0.20 |
| Seven Herbs Extract | 0.10 |
| FD&C Blue No. 1 | 0.00005 |
| D&C Yellow No. 10 | 0.0002 |
| Jojoba oil | 0.010 |
| PEG-40 Hydrogenated Castor Oil | 0.10 |
| PEG-7 Glyceryl Cocoate | 0.60 |
| Hydrogenated Castor Oil | 0.10 |
| Comperlan 100 [5] | 0.45 |
| Polyquaternium-10 | 0.080 |
| Cocamidopropyl betaine, 37% | 4.0 |
| Sodium chloride | 1.1 |
| 1,2-propanediol | 0.010 |
| Perfume | 0.30 |
| Water | Ad 100 |

[1] preferably selected from allkyl(ether)sulfates having 8 to 18 carbon atoms in the alkyl chain and 1 to 6 ethylene oxide units, particularly sodium lauryl ether sulfate with 2 ethylene oxide units,
[2] preferably selected from a mixture of $C_{8-18}$-alkylamido-($C_{1-4}$-alkyl)betaines and $C_{10}$-$C_{18}$-alkylamphoacetates and -diacetates, particularly from a mixture of $C_{8-18}$-alkylamidopropylbetaine and disodium-$C_{10}$-$C_{18}$-alkylamphodiacetate,
[3] INCI: Aqua (Water), Glycol Distearate, Glycerin, Laureth-4, Cocamidopropyl betaine, formic acid, from about 41-about 45 wt. % in water (BASF),
[4] INCI: Hydrolyzed Keratin, from about 20-about 23 wt. % in water (BASF),
[5] INCI: Cocamide MEA (BASF)

The inventive conditioning and the inventive cleaning cosmetic agents both achieved improved hair sensory characteristics and increased hair volume with use on the hair. Furthermore, the long-lasting hold of the hair volume was improved. The hair was easy to untangle, supple, and without a weighted effect after treatment. Furthermore, use of the hydrophobic fumed silica did not negatively change the texture of these agents. Accordingly, incorporation of the hydrophobic fumed silica achieved an improvement of the hair volume without negatively influencing the texture or the conditioning and/or cleaning effect of the inventive agents.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:
1. A method comprising the step of:
cleaning hair with a cosmetic composition, wherein the cosmetic composition is a shampoo, and wherein the cosmetic composition consists of:
sodium lauryl ether sulfate;
$C_{8-18}$-alkylamidopropylbetaine;
disodium-$C_{10}$-$C_{18}$-alkylamphodiacetate;
hydrophobic fumed silica;
sodium hydroxide;
citric acid;
sodium benzoate;
provitamin B5, also referred to as D-panthenol;
water;
glycol distearate;
glycerin;
laureth-4;
cocamidopropyl betaine;
formic acid;
glycine;
hydrolyzed keratin;
extracts of herbs;
dyes;
jojoba oil;

PEG-40 hydrogenated castor oil;
PEG-7 glyceryl cocoate;
hydrogenated castor oil;
cocamide MEA;
polyquaternium-10;
sodium chloride;
1,2-propanediol; and
perfumes.

2. A cosmetic agent wherein the cosmetic agent is a shampoo, and wherein the cosmetic agent consists of:
sodium lauryl ether sulfate;
$C_{8-18}$-alkylamidopropylbetaine;
disodium-$C_{10}$-$C_{18}$-alkylamphodiacetate;
hydrophobic fumed silica;
sodium hydroxide;
citric acid;
sodium benzoate;
provitamin B5, also referred to as D-panthenol;
water;
glycol distearate;
glycerin;
laureth-4;
cocamidopropyl betaine;
formic acid;
glycine;
hydrolyzed keratin;
extracts of herbs;
dyes;
jojoba oil;
PEG-40 hydrogenated castor oil;
PEG-7 glyceryl cocoate;
hydrogenated castor oil;
cocamide MEA;
polyquaternium-10;
sodium chloride;
1,2-propanediol; and
perfumes.

3. The cosmetic agent according to claim 2, wherein the cosmetic agent comprises:
the sodium lauryl ether sulfate at 8.7 weight percent;
a combination of the $C_{8-18}$-alkylamidopropylbetaine and the disodium-$C_{10}$-$C_{18}$-alkylamphodiacetate at about 6.0 weight percent; and
the hydrophobic fumed silica at about 1.0 weight percent, wherein the weight percents are based on a total weight of the cosmetic agent.

4. A cosmetic agent wherein the cosmetic agent is a conditioner, wherein the cosmetic agent consists of:
behentrimonium chloride;
N-[3-(dimethylamino)propyl]octadecanamide;
hydrophobic fumed silica;
cetearyl alcohol;
glyceryl stearate;
isopropyl myristate;
citric acid;
sodium methylparaben;
polyquaternium-37;
dicaprylyl carbonate;
lauryl glucoside;
hydrolyzed keratin;
glycine;
provitamin B5, also referred to as D-panthenol;
glycerin;
isopropanol;
perfume; and
water.

5. The cosmetic agent according to claim 4, wherein the cosmetic agent comprises:
the behentrimonium chloride at about 1.8 weight percent;
the N-[3-(dimethylamino)propyl]octadecanamide at about 0.4 weight percent; and
the hydrophobic fumed silica at about 1.0 weight percent, wherein the weight percents are based on a total weight of the cosmetic agent.

6. The cosmetic agent according to claim 3, wherein the cosmetic agent comprises:
the citric acid at about 0.4 weight percent;
the sodium benzoate at about 0.5 weight percent;
the glycine at about 0.2 weight percent;
the PEG-40 Hydrogenated Castor Oil at about 0.1 weight percent;
the PEG-7 Glyceryl Cocoate at about 0.6 weight percent;
the Hydrogenated Castor Oil at about 0.1 weight percent;
the Polyquaternium-10 at about 0.8 weight percent;
the Sodium chloride at about 1.1 weight percent; and
the 1,2-propanediol at about 0.01 weight percent, where all weight percents are based on the total weight of the cosmetic agent.

* * * * *